(12) United States Patent
Kono et al.

(10) Patent No.: US 12,298,227 B2
(45) Date of Patent: May 13, 2025

(54) OPTICAL ANALYSIS SYSTEM AND CONTROL METHOD OF OPTICAL ANALYSIS SYSTEM

(71) Applicant: Hitachi, Ltd., Tokyo (JP)

(72) Inventors: Shunsuke Kono, Tokyo (JP); Takuya Kambayashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 189 days.

(21) Appl. No.: 18/021,376

(22) PCT Filed: Sep. 24, 2021

(86) PCT No.: PCT/JP2021/035199
§ 371 (c)(1),
(2) Date: Feb. 14, 2023

(87) PCT Pub. No.: WO2022/075098
PCT Pub. Date: Apr. 14, 2022

(65) Prior Publication Data
US 2024/0035956 A1 Feb. 1, 2024

(30) Foreign Application Priority Data
Oct. 9, 2020 (JP) .................. 2020-170984

(51) Int. Cl.
*G01N 21/05* (2006.01)
*C12M 1/00* (2006.01)
(Continued)

(52) U.S. Cl.
CPC ............. *G01N 21/05* (2013.01); *C12M 41/48* (2013.01); *G01N 21/11* (2013.01); *C12M 29/00* (2013.01)

(58) Field of Classification Search
CPC ............... G01N 21/05; G01N 21/11; G01N 2021/0325; C12M 1/3446; C12M 1/3469;
(Continued)

(56) References Cited

U.S. PATENT DOCUMENTS

2009/0326827 A1* 12/2009 Mostowfi .......... B01L 3/502784
702/12
2016/0115787 A1* 4/2016 Mostowfi ............ B01F 33/3022
166/162
(Continued)

FOREIGN PATENT DOCUMENTS

JP 2016-523551 A 8/2016
JP 2019-095382 A 6/2019

*Primary Examiner* — Kara E. Geisel
*Assistant Examiner* — Jonathon Cook
(74) *Attorney, Agent, or Firm* — Procopio, Cory, Hargreaves & Savitch LLP (57) ABSTRACT

An object of the present invention is to realize an optical analysis system that enables long-term analysis by reducing the amount of liquid used for analysis. The optical analysis system includes: a first flow channel for transporting a liquid in a container; a branching medium for alternately outputting the liquid and the gas in the first flow channel; a third flow channel for transporting the liquid and the gas flowing out from the branching medium; an analysis cell into which the liquid and the gas in the third flow channel flow; a fourth flow channel that is connected to the analysis cell to discharge the liquid and the gas after passing through the analysis cell; a pump for transporting the liquid and the gas; and a control device. Then, the control device sets a reference liquid amount that is a reference required for analysis, and controls the branching medium and the pump to make the liquid and the gas alternately flow into the third flow channel. The amount of gas flowing into the third flow channel is made larger than the amount of liquid.

8 Claims, 7 Drawing Sheets

(51) Int. Cl.
*C12M 1/36* (2006.01)
*G01N 21/11* (2006.01)

(58) Field of Classification Search
CPC .... C12M 1/3476; C12M 23/16; C12M 25/01; C12M 29/00; C12M 41/48
See application file for complete search history.

(56) References Cited

U.S. PATENT DOCUMENTS

| | | | |
|---|---|---|---|
| 2016/0168524 A1* | 6/2016 | Garnica Rodriguez | ................... C12M 25/01 435/256.1 |
| 2019/0162654 A1* | 5/2019 | Noguchi | ................ G01N 21/27 |
| 2019/0302006 A1* | 10/2019 | Kono | .................. G01N 21/255 |
| 2019/0302017 A1* | 10/2019 | Kambayashi | .......... G01N 21/15 |

* cited by examiner

OPTICAL ANALYSIS SYSTEM AND CONTROL METHOD OF OPTICAL ANALYSIS SYSTEM

CROSS-REFERENCE TO RELATED APPLICATIONS

This application is a US national stage application of International Application PCT/JP2021/035199, filed Sep. 24, 2021, and claims priority to Japanese Patent Application No. 2020-170984, filed Oct. 9, 2020, the contents of which are incorporated by reference.

TECHNICAL FIELD

The present invention relates to an optical analysis system and a control method of an optical analysis system.

BACKGROUND ART

In order to grasp the progress of chemical reactions or cultures, a liquid in a container in which the chemical reactions or cultures are taking place is taken out as a liquid sample, and the components of the liquid are optically analyzed. For the optical analysis of the liquid, a method and the like is used in which the liquid to be optically analyzed is taken out from a container (for example, a reaction chamber) by using a flow channel and spectroscopic analysis is performed by using an optical measurement signal obtained by a measurement unit provided in the flow channel.

As a prior art for such optical analysis, a technique disclosed in JP 2019-95382 A (Patent Document 1) is known. In the abstract of Patent Document 1, "an optical analyzer includes: a flow channel which is connected to a container and through which a first substance flows; an introduction portion which is provided in the flow channel and through which at least two second substances are introduced into the flow channel to separate the first substance flowing through the flow channel; and a measurement unit that is provided in the flow channel and performs measurement by emitting light to the first substance and the second substance flowing through the flow channel" is described.

CITATION LIST

Patent Document

Patent Document 1: JP 2019-95382 A

SUMMARY OF THE INVENTION

Problems to be Solved by the Invention

In the technique of Patent Document 1 described above, the introduction portion is provided in the middle of the flow channel attached to the container containing the liquid, gas (such as air) is introduced before and after the liquid sample in the flow channel by the introduction portion, the liquid sample is supplied to a measurement unit (measurement module) in a state in which the liquid sample is separated from the gas, and optical analysis of the liquid is performed. Therefore, even if the composition of the liquid in the container changes with time, the composition of the liquid at each sampling time can be analyzed more accurately.

However, in the device of Patent Document 1, no consideration has been given to reducing the consumption of the liquid used for analysis. For this reason, when the optical analysis is continued for a long period of time, the amount of liquid in the container is reduced, so that it becomes difficult to analyze changes over time when the analysis is performed for a long period of time.

Therefore, the present invention has been made in order to solve such a problem, and it is an object of the present invention to provide an optical analysis system and a control method of an optical analysis system that enable long-term analysis by reducing the consumption of liquid used for measurement.

Solutions to Problems

As an example of the present invention, there is provided an optical analysis system including: a first flow channel for transporting a liquid in a container; a branching medium through which a gas is flowable and which is connected to the first flow channel to allow inflow of the liquid in the first flow channel and which makes the liquid or the gas flow out selectively; a third flow channel that is connected to the branching medium to transport the liquid and the gas flowing out from the branching medium; an analysis cell that is connected to the third flow channel so that the liquid and the gas are transported through the third flow channel; a fourth flow channel that is connected to the analysis cell to discharge the liquid and the gas after passing through the analysis cell; a pump for transporting the liquid and the gas flowing into each flow channel; and a control device that performs optical analysis by using an optical measurement signal obtained by emitting light to the liquid transported to the analysis cell. The control device sets a reference liquid amount required for analysis, and controls the branching medium and the pump to make the liquid flow into the third flow channel by the reference liquid amount and then make the gas, of which an amount is larger than an inflow amount of the liquid, flow into the third flow channel.

In addition, as another example of the present invention, there is provided a control method of an optical analysis system that includes a first flow channel for transporting a liquid in a container, a branching medium through which a gas is flowable and the liquid in the first flow channel is flowable and which makes the liquid or the gas flow out selectively, a third flow channel connected to the branching medium for inflow of the liquid and the gas, an analysis cell connected to the third flow channel for inflow of the liquid and the gas from the third flow channel, a fourth flow channel connected to the analysis cell to discharge the liquid and the gas after passing through the analysis cell, and a pump for transporting the liquid and the gas flowing into each flow channel and that performs optical analysis by using an optical measurement signal obtained by emitting light to the liquid that has flowed into the analysis cell. The control method includes: controlling the branching medium and the pump to make the liquid and the gas alternately flow into the third flow channel and setting a reference liquid amount serving as a reference; and performing control so that the liquid flows into the third flow channel by the reference liquid amount and then the gas, of which an amount is larger than an inflow amount of the liquid, flows into the third flow channel.

Effects of the Invention

According to the present invention, it is possible to provide an optical analysis system and a control method of an optical analysis system that enable long-term analysis by reducing the consumption of liquid used for analysis.

Issues, configurations, and effects other than those described above will be clarified by the description of the following embodiments.

MODE FOR CARRYING OUT THE INVENTION

Hereinafter, embodiments of the present invention will be described in detail with reference to the diagrams. In addition, it should be noted that the present invention is not limited to the embodiments described below. In addition, in each diagram in the following description, the same reference numerals (numbers) are used for each common device and equipment, and descriptions of each device and equipment that have already been described may be omitted in order to reduce repeated descriptions.

First Embodiment

Figure 1:
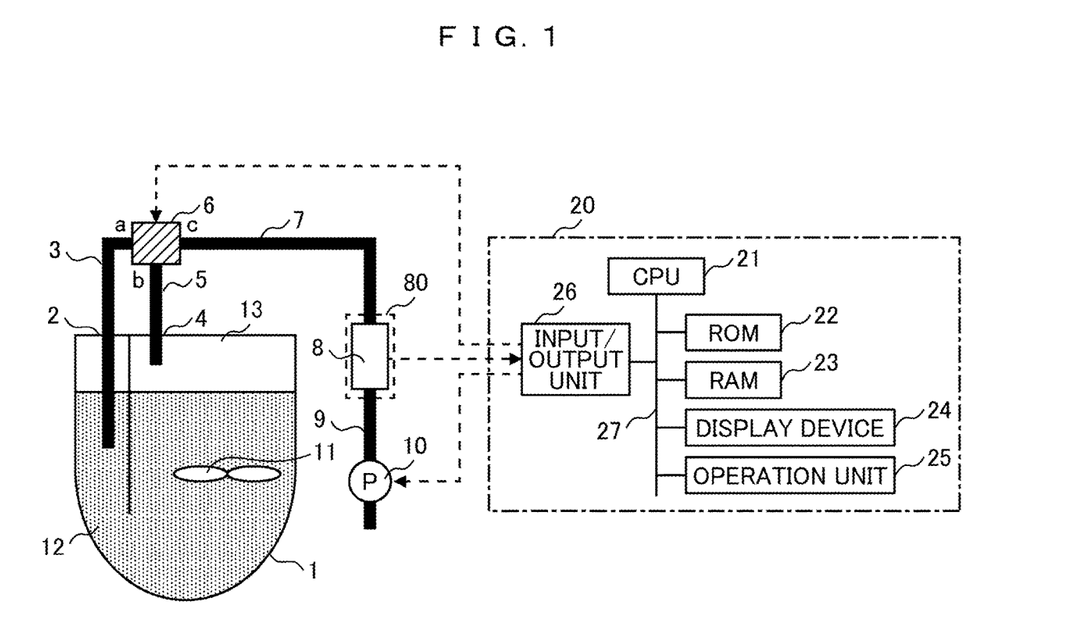
FIG. 1 is a diagram showing the configuration of an optical analysis system in a first embodiment of the present invention.
Figure 2:
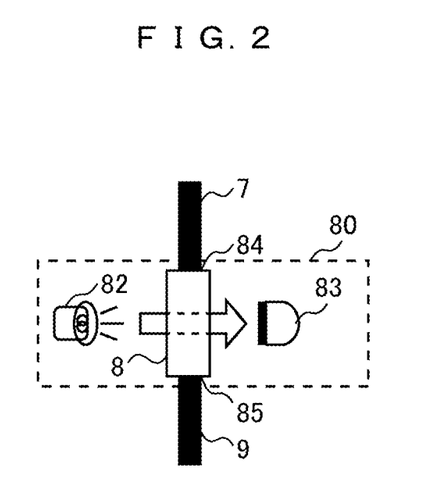
FIG. 2 is a diagram showing an overview of an analysis cell and a measurement module in the first embodiment.
Figure 3:
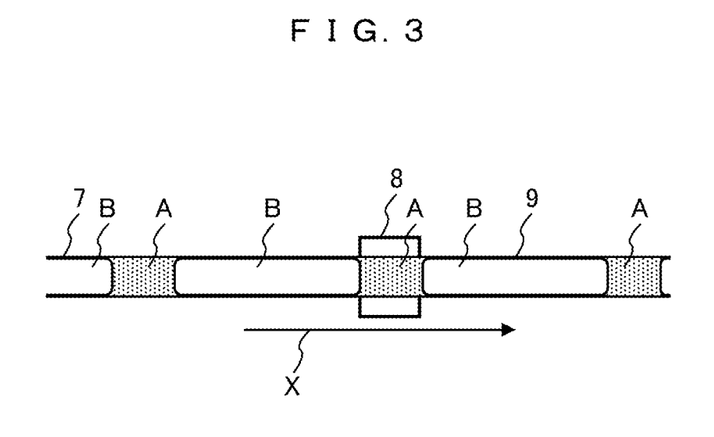
FIG. 3 is a diagram for explaining the states of liquid and gas in a flow channel.
Figure 4:
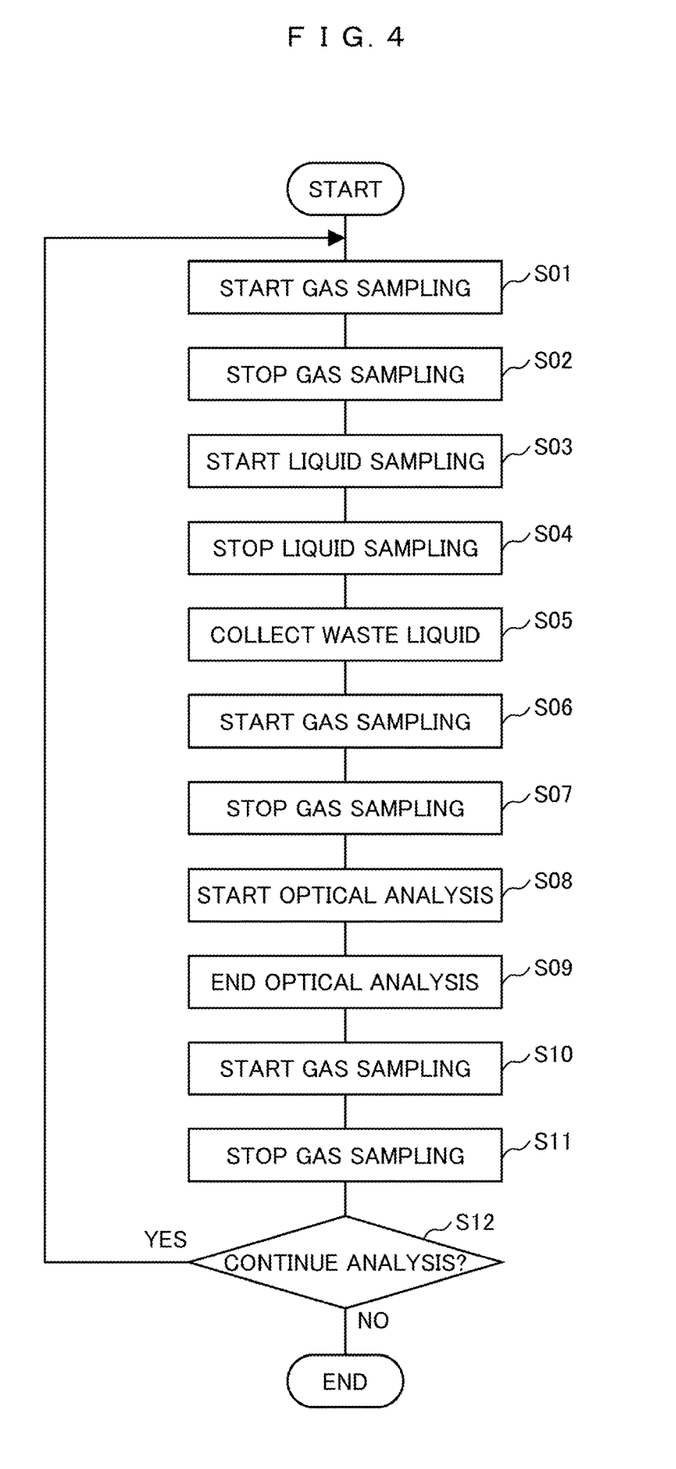
FIG. 4 is a diagram showing an operation flow in the first embodiment of the present invention.

First, a first embodiment of the present invention will be described with reference to FIGS. 1 to 4. FIG. 1 is a diagram showing the configuration of an optical analysis system in the first embodiment. FIG. 2 is a diagram showing an overview of an analysis cell and measurement module. FIG. 3 is a diagram for explaining the states of liquid and gas in a flow channel in the first embodiment. FIG. 4 is a diagram showing an operation flow in the first embodiment.

First, the configuration of the optical analysis system according to the first embodiment will be described. In FIG. 1, 1 indicates a reaction chamber, which is a type of container that contains a liquid 12. The reaction chamber 1 is a container for performing reaction of the contained liquid, and accelerates the reaction of the liquid 12 while stirring the liquid 12 with a stirring blade 11 rotated by a motor (not shown). The reaction chamber 1 includes a liquid outlet 2 and a gas outlet 4. Candidates for the reaction chamber 1 include, for example, a reaction chamber for generating substances by chemical reactions and a culture chamber for culturing cells, microorganisms, fungi, and the like.

In addition, 3 is a first flow channel. In this embodiment, a tube is used as a flow channel. For this reason, the first flow channel is hereinafter referred to as a first tube 3. The first tube 3 is connected to a branching medium 6, and extracts the liquid 12 in the reaction chamber 1 for measurement and transports the liquid 12 to the branching medium 6. Similarly, 5 is a second flow channel, which is hereinafter referred to as second tube 5. The second tube 5 is connected to a branching medium 6, and causes a gas in the reaction chamber 1 to flow into the branching medium 6. 7 is a third flow channel, which is hereinafter referred to as a third tube 7. The third tube 7 is connected to the branching medium 6, and is provided to transport the liquid and gas flowing out from the branching medium 6 to an analysis cell 8. In addition, 9 is a fourth flow channel, which is hereinafter referred to as a fourth tube 9. The fourth tube 9 is connected to the discharge side of the analysis cell 8, and is provided to discharge the liquid and gas after passing through the analysis cell 8 to the outside. Each of the first tube 3, the second tube 5, the third tube 7, and the fourth tube 9 is preferably formed of an elastic material. For example, a silicon tube, a Tygon tube, and the like can be used.

6 is a branching medium, which is connected to the first tube 3 through a first input port a so that the liquid 12 in the reaction chamber 1 can flow thereinto and which is connected to the second tube 5 through a second input port b so that a gas 13 in the reaction chamber 1 can flow thereinto. The branching medium 6 is provided to cause either the liquid or the gas to flow out from an output port c into the third tube 7 by switching the flow channel according to the control signal of a control device to be described later. In addition, the branching medium 6 is preferably formed of a material, such as a plastic that can be sterilized with gamma rays or a heat-resistant plastic that can be sterilized by an autoclave. The output port c of the branching medium 6 is connected to the analysis cell 8 through the third tube 7. Therefore, the liquid and gas flowing through the third tube 7 are transported toward the analysis cell 8 by the transporting force generated by the driving of a pump 10. The analysis cell 8 is a container provided to perform optical analysis by emitting light to a liquid sample. When a liquid (liquid sample) is transported to the analysis cell 8, a measurement module 80 emits light to the liquid and outputs an optical measurement signal after light emission. The optical measurement signal is taken into a control device 20, which will be described later. The control device 20 analyzes the liquid by using the optical measurement signal. The output side of the analysis cell 8 is connected to the fourth tube 9, so that the liquid and gas used for analysis are discharged to an external container (not shown) or the like by the transporting force of the pump 10.

FIG. 2 shows an overview of the analysis cell 8 and the measurement module 80 in the first embodiment. As shown in FIG. 2, the measurement module 80 has a light source 82 that emits light for analysis and a light receiving element 83 that receives light transmitted through the analysis cell 8. In addition, the analysis cell 8 has an inlet-side connection portion 84 and an outlet-side connection portion 85. The analysis cell 8 is preferably formed of a transparent material that does not affect the analysis. For example, in the case of analysis using near-infrared light, it is preferable that the analysis cell 8 is formed of glass, quartz, or the like. The measurement module 80 emits light from the light source 82, receives the light transmitted through the liquid present in the analysis cell 8 with the light receiving element 83, and outputs an optical measurement signal. In addition, the light received by the light receiving element 83 may be not only transmitted light but also reflected light or scattered light. The light receiving element 83 is arranged at a position suitable for receiving reflected light and scattered light.

Returning to FIG. 1, the pump 10 is provided for the inflow and transport of the liquid (liquid sample) and gas in each tube (the first tube 3, the second tube 5, the third tube 7, and the fourth tube 9). The pump 10 is preferably a pump capable of applying pressure to a tube, such as a peristaltic pump. In addition, a pump other than the peristaltic pump can be used. In this case, for example, the fourth tube 9 can be cut, and the pump 10 can be connected between the two fourth tubes 9 after cutting for use. In addition, the pump 10 can also be configured by a liquid sending unit that applies pressure to a tube to send liquid and a control device that transmits an electrical signal or the like to the liquid sending unit to instruct the liquid sending unit to operate.

Next, the control device 20 in the first embodiment will be described. First, a liquid sample supplied to the analysis cell 8 is optically measured by the measurement module 80 and an optical measurement signal is output. The control device 20 has a function (optical analysis function) of acquiring the optical measurement signal and analyzing the components of the liquid, the amount of each component, and the like. In addition, the control device 20 has a control function for controlling the branching medium 6 and the pump 10 to supply the liquid (liquid sample) and the gas to the analysis cell 8 in a state in which the liquid (liquid sample) and the gas are alternately arranged in the third tube 7. In addition, an analyzer for performing optical analysis and a device controller for controlling a device can be provided separately. However, in this embodiment, both functions are performed by one control device 20 in order to simplify the configuration.

Specifically, the control device 20 can be realized by a computer. That is, as shown in FIG. 1, the control device 20 includes a CPU (central processing unit) 21 for executing an analysis operation and a control operation, a ROM (read only memory) 22 for storing programs or information for executing the operations in the CPU 21, and a RAM (random access memory) 23 for storing information and analysis results for executing the operations in the CPU 21. In addition, the control device 20 includes a display device 24 for displaying the analysis results stored in the RAM 23, an operation unit 25 such as a keyboard for inputting data or information, an input/output unit 26 for executing signal input/output control, and a bus line 27 for signal transmission between devices.

Next, an operation of the first embodiment will be described with reference to FIGS. 1 to 4. First, in the first embodiment, a "reference liquid amount", which is the amount of liquid required for measurement in the analysis cell 8, is set, and the reference liquid amount is stored in the control device 20. Specifically, this can be realized by storing the reference liquid amount in the RAM 23 in advance. For example, the reference liquid amount is selected as the amount of liquid that fills the analysis cell 8. Specifically, it is assumed that the reference liquid amount is smaller than the capacity of the third tube 7 and larger than the capacity of the analysis cell 8.

When performing optical analysis of the liquid in the reaction chamber 1, the control device 20 drives and controls the branching medium 6 and the pump 10 to transport a liquid A (liquid sample) for analysis and a gas B, of which the amount is larger than the amount of the liquid A and which interposes the liquid A therebefore and thereafter, are alternately inserted in the third tube 7. The inflow amount is controlled so that the amount of liquid A becomes the stored reference liquid amount. That is, the first input port a and the output port c of the branching medium 6 are controlled to communicate with each other, and the pump 10 is driven to extract the liquid in the reaction chamber 1 in an amount that matches the reference liquid amount and make the extracted liquid flow into the third tube 7. Then, the control device 20 makes the second input port b and the output port c of the branching medium 6 communicate with each other, and drives the pump 10 so that the gas 13 in the reaction chamber 1 flows into the third tube 7 in an amount larger than the reference liquid amount. In order to continue the analysis of the liquid further after the end of the inflow of the gas, the inflow of the liquid A is controlled in the same manner as described above. As a result, in the third tube 7, the liquid A and the gas B whose amount is larger than the amount of the liquid A are alternately arranged. In addition, for a period during which the analysis is not continued, the state described above does not necessarily have to be maintained.

The state of the third tube 7 is shown in FIG. 3. As can be seen from FIG. 3, in the third tube 7, the liquid A that is introduced so as to be adjusted to the reference liquid amount, which is a minimum liquid amount required for measurement, and the larger amount of gas B than the liquid amount are alternately arranged. Here, the reference liquid amount (volume) is selected so as to be smaller than the capacity of the third tube 7 and larger than the capacity of the analysis cell 8. The amount of gas B in the third tube 7 is selected to be, for example, several times the amount of liquid A (reference liquid amount). By introducing a large amount of gas, the liquid A is transported toward the analysis cell by that amount. The liquid A and the gas B in such a state are transported to the analysis cell 8 by driving the pump 10. That is, by driving the pump 10, the atmospheric pressures of the fourth tube 9, the analysis cell 8, and the third tube 7 are reduced to move the liquid sample to the analysis cell 8. This movement processing is performed in a state in which gas insertion through the branching medium 6 is allowed. In addition, the arrow X indicates the transport (transfer) direction of the liquid A and the gas B.

Here, as shown in FIG. 1, in the first embodiment, the gas 13 in the reaction chamber 1 is used as the gas B supplied into the third tube 7. This is to transport the liquid A to the analysis cell and perform measurement while maintaining the state in the reaction chamber 1 as the state of the liquid used for measurement as much as possible. That is, for example, the PH of the liquid in the reaction chamber 1 is adjusted with carbon dioxide. In such a case, when the outside air outside the reaction chamber 1 is used as the gas B, the conditions inside the reaction chamber 1 and the conditions inside the third tube 7 become different environments. On the other hand, when the gas 13 in the reaction chamber 1 is used as a gas to flow into the third tube 7, the extracted liquid can be supplied to the analysis cell 8 while maintaining the same state as in the reaction chamber 1. In the first embodiment, such a configuration is adopted to realize more accurate liquid analysis.

The liquid A and the gas B are transported to the analysis cell 8 in a state in which the liquid A and the gas B are alternately arranged. However, as shown in FIG. 3, when the liquid A reaches the analysis cell 8 and the inside of the analysis cell 8 is filled with the liquid A, which is a liquid sample, the pump 10 is temporarily stopped. Then, the measurement module 80 performs measurement in this state and outputs an optical measurement signal. The control device 20 acquires the optical measurement signal to obtain the liquid analysis result, and stores the liquid analysis result in the RAM 23. For the optical analysis performed by using the analysis cell 8, for example, spectroscopic analysis methods using infrared rays, near-infrared rays, visible rays, ultraviolet rays, fluorescence, X-rays, and the like are used. The control device 20 starts an analysis program stored in the ROM 22 to analyze the optical measurement signal, and stores the analysis result in chronological order. In addition, this result can be displayed on the display device 24.

After the end of the acquisition of the measurement signal, the liquid A and the gas B are transported through the fourth tube 9 and discharged to the outside by driving the pump 10.

Subsequently, a detailed control operation flow in the control device 20 will be described with reference to FIG. 4. In FIG. 4, in step S01, the second input port b and the output port c of the branching medium 6 are made to communicate with each other so that the second tube 5 and the third tube 7 are connected to each other. In this state, the pump 10 is driven to make the gas 13 in the reaction chamber 1 flow into the third tube 7. That is, by driving the pump 10, the internal pressures of the second tube 5, the third tube 7, and the fourth tube 9 are changed to introduce the gas 13 in the reaction chamber 1 into the tubes.

When the inflow (introduction) of the gas in step S01 reaches a predetermined amount, the process proceeds to step S02 to stop the absorption of the gas. Sampling is stopped by stopping the pump 10 in a state in which the second tube 5, the third tube 7, and the fourth tube 9 are sufficiently filled with the gas inside the reaction chamber 1.

After this step S02, the process proceeds to step S03. In step S03, the first input port a and the output port c of the branching medium 6 are made to communicate with each other by a control signal from the control device 20 so that the first tube 3 and the third tube 7 are connected to each other. In this state, the control device 20 starts the pump 10 to change the internal pressures of the first tube 3, the third tube 7, and the fourth tube 9. As a result, the liquid inside the reaction chamber 1 starts to flow from the first tube 3 into the third tube 7 through the branching medium 6.

In step S04, when the third tube 7 is filled with the liquid A by the reference liquid amount required for measurement, the pump 10 is stopped to stop the absorption of the liquid. Whether or not the third tube 7 is filled with the liquid A by the reference liquid amount can be determined, for example, by attaching an optical sensor or a pressure sensor to the third tube 7 and monitoring the output of the sensor by the control device 20. The inside of the third tube 7 may be visually checked.

In step S05, the first input port a and the second input port b of the branching medium 6 are made to communicate with each other, so that the liquid remaining in the first tube 3 is returned to the reaction chamber 1 through the second tube 5.

Then, in step S06, the second input port b and the output port c of the branching medium 6 are controlled so as to communicate with each other, so that the gas B in the reaction chamber 1 flows from the second tube 5 into the third tube 7. That is, the gas in the reaction chamber 1 enters the second input port b of the branching medium 6 from the second tube 5 and flows into the third tube 7 from the output port c. The transporting force of the gas B is generated by operating the pump 10 to change the internal pressures of the second tube 5, the third tube 7 and the fourth tube 9. As the gas B is transported, the liquid A in the third tube 7 that has flowed thereinto earlier is transported toward the analysis cell 8. This transportation continues until the timing when the liquid A reaches the analysis cell 8.

In step S07, the pump 10 is stopped when the liquid A reaches the analysis cell 8 and the analysis cell 8 is filled with the liquid A. At this point in time, the liquid A (sampling liquid) for measurement stays in the analysis cell 8. In this state, the liquid A can be measured by an analysis module 80. In addition, if the speed of circulation of the liquid sample (liquid A) is sufficiently slow so that the liquid sample stays in the analysis cell 8 for a longer time than the time required for measurement, it is not necessary to stop the pump 10.

In step S08, optical analysis is started. The analysis module 80 outputs an optical measurement signal (such as an absorbance spectrum). The optical measurement signal is taken into the control device 20.

In step S09, the control device 20 acquires the optical measurement signal, performs optical analysis, and ends the optical analysis.

In step S10, the second input port b and the output port c of the branching medium 6 are made to communicate with each other so that the flow of the gas in the reaction chamber 1 to the third tube 7 starts. This is to discharge the liquid A used for measurement in the analysis cell to the outside through the fourth tube 9. By operating the pump 10 to change the internal pressures of the second tube 5, the third tube 7, and the fourth tube 9, the liquid A is discharged to the outside of the fourth tube 9 together with the gas B. The discharged liquid is stored in an external container (not shown in FIG. 1). In addition, it is also possible to return the liquid to the reaction chamber 1.

In step S11, the operation of the pump 10 is stopped when the liquid A supplied for measurement is discharged to the outside of the fourth tube 9.

Then, the process proceeds to step S12 to determine whether or not to continue the analysis. If the analysis is to be continued further (YES in step S12), the process returns to step S01 to repeat the above-described operations. If not continued (NO in step S12), the operation ends. In this manner, the analysis is repeated as many times as required depending on the required analysis frequency.

Effect of the First Embodiment

According to the first embodiment of the present invention described above, the reference liquid amount required for analysis is set, the amount of liquid is extracted, and the liquid is supplied to the analysis cell by the gas, of which the amount is larger than the amount of the liquid and which interposes the liquid therebefore and thereafter, to perform optical analysis. Therefore, since the amount of liquid used for measurement is limited to the necessary amount, it is possible to save liquid consumption. In addition, since the volume of the gas in the third tube is larger than the volume of the liquid, it is possible to reliably reduce problems such as mixing of the liquid A with the liquid A to be sampled next.

In addition, in the first embodiment, the gas in the reaction chamber 1 is used as a gas used together with the liquid. With this configuration, since there is no environmental difference between the state of the liquid in the reaction chamber 1 and the state of the liquid for measurement, the extracted liquid can be transported to the analysis cell 8 for measurement while maintaining the same state as in the reaction chamber 1. As a result, more accurate liquid analysis can be performed.

Second Embodiment

Next, a second embodiment will be described with reference to FIG. 5. Since the basic configuration of the second embodiment is the same as that of the first embodiment, the description of the functions or operations of the devices that have already been described will be omitted. Here, the description will be focused on a part of the second embodiment different from the first embodiment.

Figure 5:
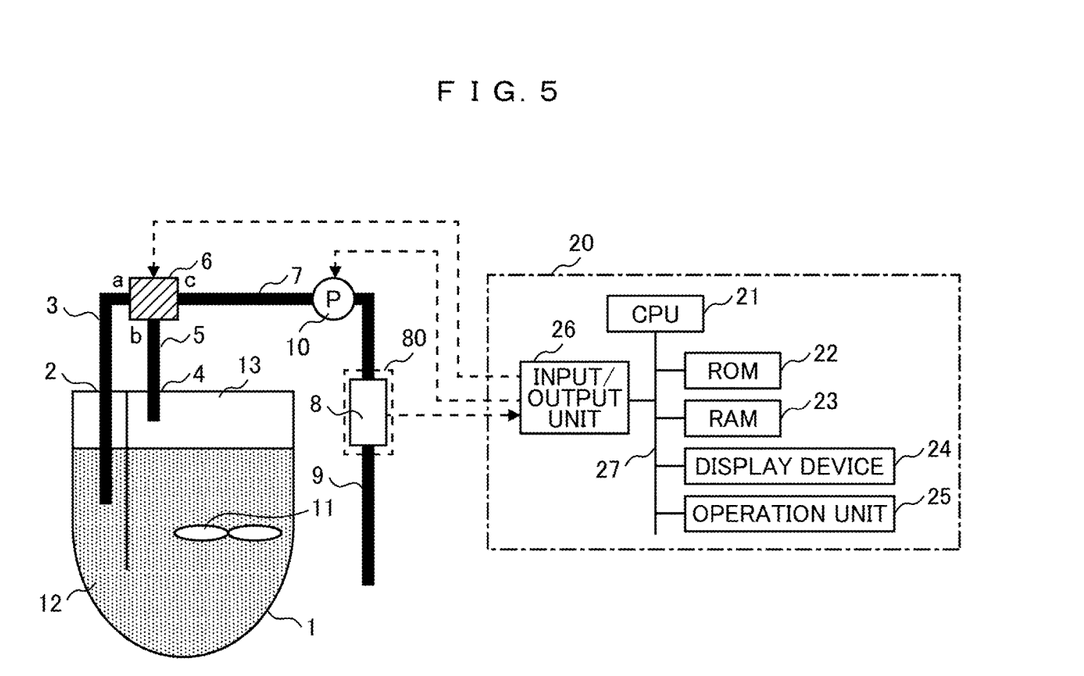
FIG. 5 is a diagram showing the configuration of an optical analysis system in a second embodiment of the present invention.

The second embodiment shown in FIG. 5 and the first embodiment shown in FIG. 1 have the same configuration except that the mounting position of the pump 10 is different. That is, in the case of FIG. 1, the pump 10 is installed in the middle of the fourth tube 9. On the other hand, in the second embodiment shown in FIG. 5, the pump 10 is installed in the middle of the third tube 7. In the second embodiment, when sampling the liquid A (liquid sample), first, the control device causes a liquid sample of the reference liquid amount to be absorbed into the third tube 7 through the first tube 3 by driving the pump 10 in a state in which gas insertion through the branching medium 6 is stopped. Here, it is assumed that the reference liquid amount is smaller than the capacity of the third tube 7 and larger than the capacity of the analysis cell 8. Then, the control device 20 drives the pump 10 in a state in which gas insertion through the branching medium 6 is allowed, thereby performing control to move the liquid sample to the analysis cell 8 while increasing the volume of the gas between the liquid sample in the third tube 7 and the branching medium 6.

The second embodiment also has the same effect as the first embodiment.

Third Embodiment

Next, a third embodiment will be described with reference to FIG. 6. The basic configuration of the third embodiment is similar to that of the first embodiment shown in FIG. 1. Therefore, the content already described will be omitted, and the description will be focused on a part of the third embodiment different from the first embodiment.

Figure 6:
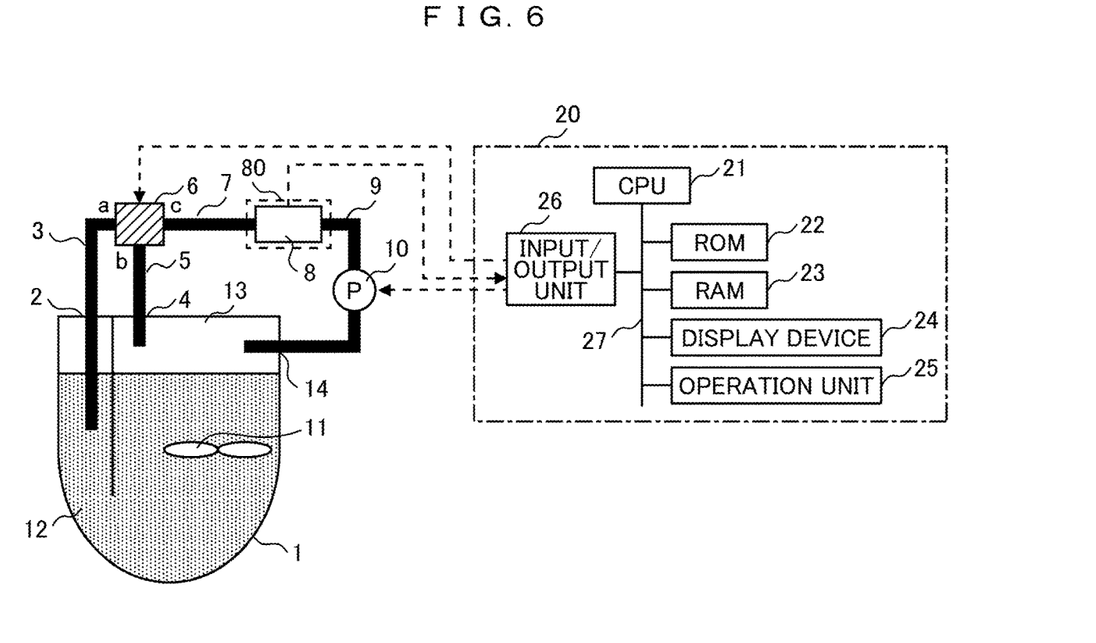
FIG. 6 is a diagram showing the configuration of an optical analysis system in a third embodiment of the present invention.

In FIG. 6, a discharge side end portion of the fourth tube 9 communicates with the inside of the reaction chamber 1 through an inlet 14. With this configuration, the liquid A and the gas B used for measurement in the analysis cell 8 can pass through the fourth tube 9 and be returned into the reaction chamber 1. When returning the liquid to the reaction chamber 1, a filter (not shown) can be provided as necessary to remove impurities and the like contained in the liquid.

According to the third embodiment, the same effect as in the first embodiment is obtained, and the reduction of the liquid in the reaction chamber 1 is almost eliminated because the liquid after measurement is collected in the reaction chamber 1.

Fourth Embodiment

Figure 7:
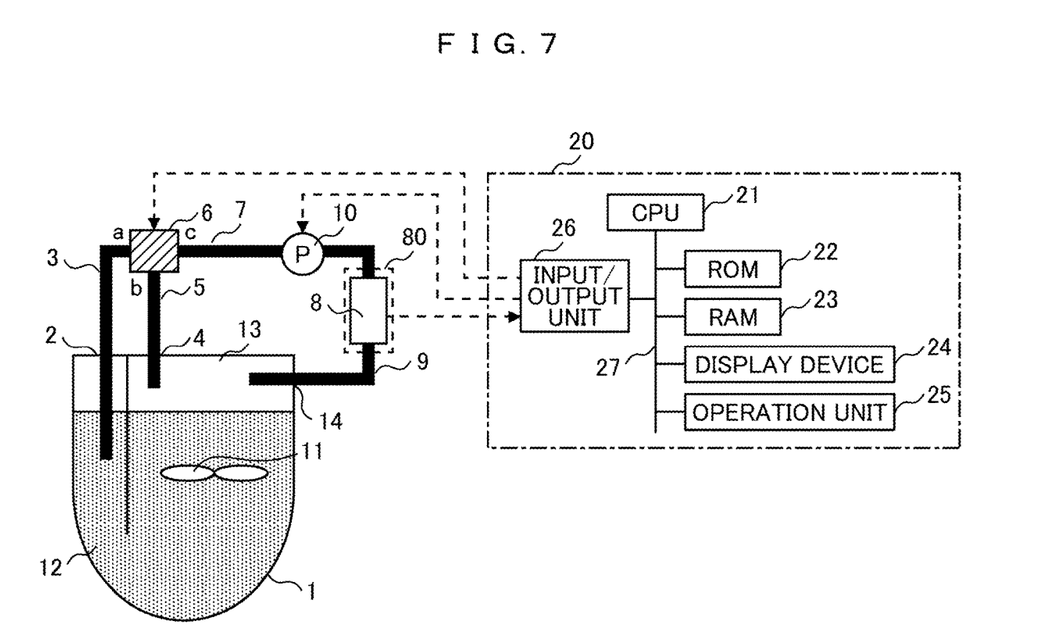
FIG. 7 is a diagram showing the configuration of an optical analysis system in a fourth embodiment of the present invention.

Next, a fourth embodiment will be described with reference to FIG. 7. The fourth embodiment has almost the same configuration as the third embodiment except for the installation position of the pump 10. That is, in the case of FIG. 6 that is the third embodiment, the pump 10 is installed in the middle of the fourth tube 9. On the other hand, in the fourth embodiment shown in FIG. 7, the pump 10 is installed in the middle of the third tube 7.

According to the fourth embodiment, the same effect as in the third embodiment is obtained.

Other Embodiments

While Although the invention made by the inventor has been specifically described above based on the embodiments, the invention is not limited to the above embodiments, and can be variously modified without departing from the gist of the invention. For example, the above embodiments have been described in detail for easy understanding of the present invention, but the present invention is not necessarily limited to having all the components described above. In addition, some of the components in one embodiment can be replaced with the components in another embodiment, and the components in another embodiment can be added to the components in one embodiment.

REFERENCE SIGNS LIST

1 Reaction chamber
2 Liquid outlet
3 First tube
4 Gas outlet
5 Second tube
6 Branching medium
7 Third tube
8 Analysis cell
9 Fourth tube
10 Pump
11 Stirring blade
12 Liquid
13 Gas
14 Inlet
20 Control device
21 CPU
22 ROM
23 RAM
24 Display device
25 Operation unit
26 Input/output unit
80 Measurement module
82 Light source
83 Light receiving element

The invention claimed is:
1. An optical analysis system, comprising:
a first flow channel for transporting a liquid in a container;
a branching medium through which a gas is flowable and which is connected to the first flow channel to allow inflow of the liquid in the first flow channel and which makes the liquid or the gas flow out selectively;
a third flow channel that is connected to the branching medium to transport the liquid and the gas flowing out from the branching medium;
an analysis cell that is connected to the third flow channel so that the liquid and the gas are transported through the third flow channel;
a fourth flow channel that is connected to the analysis cell to discharge the liquid and the gas after passing through the analysis cell;
a pump for transporting the liquid and the gas flowing into each flow channel;
a processor that performs optical analysis by using an optical measurement signal obtained by emitting light to the liquid transported to the analysis cell,
wherein the processor sets a reference liquid amount required for analysis, and controls the branching medium and the pump; and
a second flow channel that causes the liquid to flow into the third flow channel by the reference liquid amount and then causes the gas, of which an amount is larger than an inflow amount of the liquid to flow into the third flow channel, and further causes the gas in the container to flow into the branching medium, wherein the reference liquid amount is selected to be less than a capacity of the third flow channel and more than a capacity of the analysis cell, and the pump is driven in a state where the gas inflow by the branching medium is stopped, and wherein the processor is programmed to control the liquid of the reference liquid amount to flow into the third flow channel via the first flow channel, and then drive the pump in a state in which gas insertion by the branching medium is permitted to move the liquid to the analysis cell.

2. The optical analysis system according to claim 1, wherein the second flow channel causes the gas in the container to flow into the branching medium.

3. The optical analysis system according to claim 1, wherein the liquid that has flowed into the fourth flow channel is collected in the container.

4. The optical analysis system according to claim 1, wherein the pump is provided in a middle of the fourth flow channel, and wherein the processor drives the pump in a state in which gas insertion through the branching medium is allowed so that atmospheric pressures of the fourth flow channel and the analysis cell are reduced.

5. The optical analysis system according to claim 1, wherein the pump is provided in a middle of the third flow channel, and wherein the processor drives the pump in a state in which gas insertion through the branching medium is allowed so that the liquid is moved to the analysis cell while increasing a volume of a gas flowing between the liquid in the third flow channel and the branching medium.

6. A control method of an optical analysis system that includes a first flow channel for transporting a liquid in a container, a branching medium through which a gas is flowable and the liquid in the first flow channel is flowable and which makes the liquid or the gas flow out selectively, a third flow channel connected to the branching medium for inflow of the liquid and the gas, an analysis cell connected to the third flow channel for inflow of the liquid and the gas from the third flow channel, a fourth flow channel connected to the analysis cell to discharge the liquid and the gas after passing through the analysis cell, and a pump for transporting the liquid and the gas flowing into each flow channel and that performs optical analysis by using an optical measurement signal obtained by emitting light to the liquid that has flowed into the analysis cell, the control method comprising:

controlling the branching medium and the pump to make the liquid and the gas alternately flow into the third flow channel and setting a reference liquid amount serving as a reference;

performing control so that the liquid flows into the third flow channel by the reference liquid amount and then controlling the gas, of which an amount is larger than an inflow amount of the liquid, to flow into the third flow channel; and providing a second flow channel for causing the gas in the container to flow into the branching medium, and controlling the gas to flow into the third flow channel, wherein the reference liquid amount is selected to be less than a capacity of the third flow channel and more than a capacity of the analysis cell, and the pump is driven in a state where the gas inflow by the branching medium is stopped, such that the liquid of the reference liquid amount flows into the third flow channel via the first flow channel, and then the pump drives in a state in which gas insertion by the branching medium is permitted to move the liquid to the analysis cell.

7. The control method of an optical analysis system according to claim 6, wherein the gas is controlled to flow into the third flow channel.

8. The control method of an optical analysis system according to claim 6, wherein the liquid that has flowed into the fourth flow channel is collected in the container.

* * * * *